United States Patent [19]

Schieferstein et al.

[11] Patent Number: 4,685,931
[45] Date of Patent: Aug. 11, 1987

[54] ACRYLATE DISPERSION AND ITS USE FOR THICKENING HYDROGEN PEROXIDE PREPARATIONS

[75] Inventors: Ludwig Schieferstein, Wuppertal; Detlef Hollenberg, Hilden; Norbert Maak, Neuss, all of Fed. Rep. of Germany

[73] Assignee: Henkel Kommanditgesellschaft auf Aktien, Duesseldorf, Fed. Rep. of Germany

[21] Appl. No.: 808,591

[22] Filed: Dec. 13, 1985

[30] Foreign Application Priority Data

Dec. 14, 1984 [DE] Fed. Rep. of Germany ....... 3445549

[51] Int. Cl.$^4$ .................... A61K 7/13; A61K 7/135; C08L 31/00; C08L 33/06
[52] U.S. Cl. ............................. 8/406; 8/407; 252/174.24; 252/186.29; 252/186.43; 524/559; 524/560
[58] Field of Search ......... 524/559, 560, 561; 526/317; 8/406, 407; 252/174.24, 186.29, 186.43

[56] References Cited

U.S. PATENT DOCUMENTS

| 3,122,417 | 1/1962 | Blaser et al. | 23/207.5 |
| 3,884,627 | 5/1975 | Brody et al. | 8/10.2 |
| 3,894,980 | 6/1975 | DeTommaso | 260/29.6 RW |
| 3,993,612 | 11/1976 | Aihara et al. | 260/23.7 A |
| 4,130,501 | 12/1978 | Lutz et al. | 252/186 |
| 4,139,514 | 2/1979 | Bassett | 524/831 |
| 4,311,478 | 1/1982 | Bugaut et al. | 8/407 |
| 4,313,932 | 2/1982 | Watts | 424/62 |
| 4,323,360 | 4/1982 | Bugout et al. | 8/407 |
| 4,351,754 | 9/1982 | Dupré | 524/445 |
| 4,514,552 | 4/1985 | Shay et al. | 526/301 |
| 4,542,175 | 9/1985 | Fink et al. | 524/516 |

FOREIGN PATENT DOCUMENTS

| 1109132 | 6/1961 | Fed. Rep. of Germany . |
| 1164095 | 11/1971 | Fed. Rep. of Germany . |
| 870994 | 6/1961 | United Kingdom . |

Primary Examiner—Dennis L. Albrecht
Assistant Examiner—Linda Skaling
Attorney, Agent, or Firm—Ernest G. Szoke; Henry E. Millson, Jr.

[57] ABSTRACT

An aqueous dispersion of a copolymer of
from about 50 to 60% by weight ethyl acrylate
from about 30 to 40% by weight methacrylic acid
from about 5 to 15% by weight acrylic acid and
from about 0.02 to 0.04% by weight of a polyethylenically copolymerizable monomer, for example ethylene glycol dimethacrylate. The dispersion is suitable as an additive for aqueous, mildly acidic preparations of hydrogen peroxide to impart an increased viscosity to them after neutralization. The hydrogen peroxide preparations in question are particularly suitable for use as a developer composition for oxidative hair dyes and hair bleaches.

24 Claims, No Drawings

ACRYLATE DISPERSION AND ITS USE FOR THICKENING HYDROGEN PEROXIDE PREPARATIONS

BACKGROUND OF THE INVENTION

1. Field of the Invention

This invention relates to an aqueous dispersion having a solids content of from about 5 to 50% by weight of a copolymer of ethyl acrylate, methacrylic acid, acrylic acid and a polyethylenically unsaturated copolymerizable monomer. The dispersion is suitable for thickening aqueous systems, particularly hydrogen peroxide preparations of the type used as the developer composition for oxidative hair dyes and for hair bleaches.

2. Description of Related Art

It has long been known that alkali-soluble acrylate dispersions may be used for thickening aqueous systems. Dispersions having a solids content of from 25 to 50% by weight of a copolymer comprising at least 10% by weight of an acrylic acid lower alkyl ester, 25 to 70% by weight methacrylic acid and, optionally, 0 to 40% by weight of another monoethylenically unsaturated co-monomer are described, for example, in Great Britian Pat. No. 870,994. German Application No. 1,164,095 describes copolymers of 50 to 75% by weight ethyl acrylate, 25 to 35% by weight acrylic acid and 0 to 25% by weight of other co-monomers.

These publications indicate that the molecular weight of the copolymers and hence their thickening effect can be increased by the addition of a polyethylenically unsaturated copolymerizable cross-linking co-monomer. According to Great Britian No. 870,994, a cross-linking co-monomer content of from about 0.1 to 0.8% by weight and preferably from about 0.15 to 0.3% by weight of the copolymer leads to particularly favorable acrylate copolymers.

However, these known copolymer dispersions do not completely satisfy the stringent demands needed for effective thickening, particularly when the dispersions are used in cosmetic preparations. Neutralized dispersions of these copolymers, for example, often show a marked tendency towards legging, thus making them unsuitable for cosmetic applications due to the greasy feel they impart to the skin. Additionally, some dispersions show only moderate thickening power; while with other dispersions, the viscosities of the thickened preparations are extremely sensitive to other ingredients in the ultimate formation, i.e., the viscosity of the thickened preparations may be either severely reduced or possibly increased into the gel range by certain constituents of the formulation, e.g., electrolytes. With these prior art dispersions, some preparations also show an excessive and unfavorable viscosity dependence on the concentration of the thickener.

Particularly stringent demands are made of alkali-soluble acrylate copolymer dispersions used for thickening hydrogen peroxide preparations. Preparations of this type are commonly employed as developer compositions for oxidative hair dyes and for hair bleaches. The mildly acidic preparations are mixed with an alkaline dye cream just before application to the hair to form an alkaline dye preparation. Since this destroys the consistency of the cream, a thickener dispersion is included in the developer preparation in order to achieve a mixture viscosity suitable for applying the alkaline dye preparation to hair after the two components have been combined.

Even though formulations of various oxidative hair dyeing preparations may differ considerably, developer compositions—for the same dosage—should always ensure that mixtures of the dye cream and the developer composition have a proper consistency for the end use. This result is possible only if the thickener responsible for enhancing consistency is particularly effective and immune to troublesome influences.

The same can be said about hair bleaches, which also are formulated as two-component products consisting of a mildly acidic hydrogen peroxide preparation and an alkaline bleaching cream. Again, these components are mixed together before application. The compositions of the two components and their proportions in the final mixture are such that the hair bleach is alkaline after the two components have been combined. The hydrogen peroxide preparation should contain a thickener dispersion which adjusts the viscosity of the blended hair bleach to a value suitable for application to hair.

DESCRIPTION OF THE INVENTION

The present invention is directed to an aqueous dispersion of a copolymer of ethyl acrylate, methacrylic acid, acrylic acid and a polyethylenically unsaturated copolymerizable monomer. The aqueous dispersion of this invention has a solids content of from about 5 to 30% by weight, preferably 20 to 30%.

It has been found that the aqueous dispersion of the copolymer of the present invention has such a strong thickening effect for aqueous solutions, after neutralization of free carboxyl groups with water-soluble alkalis, that the thickened aqueous solutions are free from clouding and the viscosity and clear solubility are relatively stable to the effect of dissolved salts. The copolymer of this invention comprises:

from about 50 to 60% by weight ethyl acrylate
from about 30 to 40% by weight methyacrylic acid
from about 5 to 15% by weight acrylic acid and
from about 0.02 to 0.04% by weight of a polyethylenically unsaturated copolymerizable monomer.

The copolymer dispersion of the present invention typically can be used for thickening a wide variety of aqueous systems on neutralization. For example, the copolymer dispersion can be used as a replacement for known acrylate copolymer dispersions in formulations in which such dispersions have conventionally been used. Those skilled in the art will immediately recognize a large number of potential uses. The copolymer dispersion of the present invention is particularly suitable as an additive for aqueous, mildly acidic hydrogen peroxide preparations. The copolymer dispersion imparts an increased viscosity to such preparations upon neutralization, particularly neutralization to an alkaline pH-value of about 8.0.

The copolymer dispersions of the present invention are prepared using known emulsion polymerization procedures, including well-known emulsifiers and stabilizers and well-known initiators. Suitable emulsifiers and stabilizers include, for example, nonylphenoxy polyethoxy sulfosuccinates and/or alkyl polyethoxy sulfates in the form of their sodium and/or ammonium salts, as for example described in U.S. Pat. No. 3,649,581. As recognized by those skilled in this art, the emulsifiers should be used in a sufficient quantity to yield adequate particle fineness and dispersion stability. Typically, these emulsifiers can be used in an amount of from about 1 to 4% by weight, based on the aqueous dispersion itself.

Preferred free-radical initiators for use in preparing the copolymer dispersions of the present invention include such initiators as alkali metal peroxydisulfates, e.g., potassium, and ammonium peroxydisulfate (persulfates), although other known free-radical formers, such as tert-butyl hydroperoxide and cumyl hydroperoxide for example, are also suitable. Where potassium or ammonium peroxydisulfate is used, a quantity within the range of from about 0.002 to 0.01% by weight, based on the dispersion itself, is sufficient.

Copolymer dispersions of the type used in the present invention may be prepared with a solids content of up to about 50% by weight. However, it has been found that, with a lower solids content for example within the range of about 5 to 30% by weight and more preferably from about 20 to 30% by weight, the amount of coarse-particle coagulates formed is very small. Such coagulates must be removed by filtration after polymerization.

The so-called monomer input process is particularly suitable for producing the copolymer dispersion of the present invention. In this process, an aqueous solution containing about one third of the total amount of initiator to be employed and about 40% by weight of the total amount of emulsifier is prepared and is initially introduced into a reaction vessel wherein an inert gas atmosphere (e.g., carbon dioxide or nitrogen) is established over the solution. Part of the monomer mixture (e.g., about 10 to 30% of the total amount) then is introduced into the reactor, with stirring—the solution having been heated to around 70°–80° C. After the reaction has started, as evidenced by dissipation of the heat of polymerization, the rest of the monomer mixture, the remaining emulsifier and a second third of the initiator are gradually added simultaneously to the reaction vessel. Once the heat of polymerization has abated, an aqueous solution of the last third of the initiator is added to the copolymer dispersion to ensure that all of the monomers are reacted.

In addition to the main monomeric constituents, i.e., ethyl acrylate, methacrylic acid and acrylic acid, the copolymer also includes as an essential constituent a polyethylenically unsaturated copolymerizable monomer. Copolymerizable monomers which may be used in the broad practice of the present invention include compounds which contain two or more non-conjugated points of ethylenic unsaturation or two or more non-conjugated vinylidene groups of the structure, $CH_2=C=$, such as divinyltoluene, divinylbenzene, trivinylbenzene, divinylnaphthalene, ethylene glycol diacrylate or dimethacrylate, trimethylene glycol diacrylate or dimethacrylate, 2-ethylhexane-1,3-dimethacrylate, divinylxylene, divinylethylbenzene, divinyl ether, divinyl sulfone, allyl ethers of polyhydric compounds such as glycerol, pentaerythritol, sorbitol, sucrose and resorcinol, divinylketone, divinylsulfide, allyl acrylate, diallyl maleate, diallyl fumarate, diallyl phthalate, diallyl succinate, diallyl carbonate, diallyl malonate, diallyl oxalate, diallyl adipate, diallyl sebacate, diallyl tartrate, diallyl silicate, triallyl tricarballylate, triallyl aconitate, triallyl citrate, triallyl phosphate, $N,N^1$-methylene-diacrylamide, $N,N^1$-methylenedimethacrylamide, $N,N^1$-ethylidenediacrylamide and 1,2-di-(alpha-methylmethylenesulfonamide)-ethylene.

The function of the polyethylenically unsaturated copolymerizable monomer is to increase the molecular weight of the copolymer by crosslinking. Particularly suitable (di)ethylenically and (tri)ethylenically unsaturated monomers for use in the present invention are di- and tri-esters of acrylic acid and methacrylic acid, such as for example ethylene glycol dimethacrylate, trimethylolpropane trimethacrylate, polyethylene glycol (400) dimethacrylate and 2-ethylhexane-1,3-dimethacrylate, as well as esters of acrylic acid and methacrylic acid with unsaturated alcohols, such as allyl methacrylate. Diethylenically unsaturated monomers are particularly preferred.

The quantity of the polyethylenically unsaturated copolymerizable monomer used for crosslinking the copolymer has a major bearing on the properties of the copolymer dispersion of the present invention. On the one hand, using an inadequate amount of the crosslinking monomer yields a copolymer dispersion having an inadequate thickening property and a pronounced tendency towards legging. On the other hand, using an excessive amount of the crosslinking monomer causes clouding or gelation in the neutralized copolymer dispersion. Based on these competing considerations, the polyethylenically unsaturated monomer should be included in the monomer mixture and thus in the polymerized copolymer in an amount between about 0.2 to 0.04% by weight.

Particularly suitable copolymer dispersions are obtained where the copolymer consists of
approx. 55% by weight ethyl acrylate
approx. 35% by weight methacrylic acid
approx. 10% by weight acrylic acid and
approx. 0.025% by weight ethylene glycol dimethacrylate.

In aqueous solutions, the copolymer dispersions of the present invention are stable, thin liquids. They remain stable, thin liquids even in only mildly acidic aqueous solutions, i.e., solutions having a pH within the range of about 2 to 5. The polymer chains begin to unwind and the viscosity of the solutions begin to increase as the pH of the dilute aqueous solution is increased by the addition of an aqueous base. Suitable aqueous bases include for example an ammonia solution, alkali metal hydroxide solutions (for example sodium hydroxide, potassium hydroxide and the like), and water soluble amines and alkanolamines, for example methyl amine, trimethyl amine, ethyl amine, and mono-, di- or triethanolamine).

Upon adding a base to the dispersion, the carboxyl groups of the copolymer are neutralized, i.e., converted into the salt form. Neutralization is fairly rapid after the copolymer dispersions and the aqueous base have been combined. At a pH of about 8, ionization of carboxyl groups and development of viscosity are substantially complete. The viscosity of the thickened solution decreases only slightly, with the addition of more alkali, and also is largely unaffected by the addition of water-soluble salts.

The copolymer dispersion of this invention can be added to the aqueous medium to be thickened and, after thorough mixing therein, an alkaline material can be added to neutralize the acid copolymer. Also, the alkaline material could be added directly to the copolymer dispersion before it is added to the aqueous medium to be thickened. In this latter case, however, the solids content of the copolymer dispersion should be maintained below about 15%. Preferably, the aqueous medium to be thickened already contains the required alkaline material. Thus, the copolymer dispersion is automatically neutralized as it is mixed with the aqueous medium.

The copolymer dispersions of the present invention are especially suitable for producing hydrogen peroxide preparations for use as developers for oxidative hair dyes or for hair bleaches. Developer dispersions for these applications typically contain from about 1 to 20% by weight of hydrogen peroxide and from about 1 to 5% by weight (solids) of the copolymer dispersions of the present invention. Such preparations represent a preferred embodiment of the invention.

In addition to these main constituents, these developer dispersions also typically contain a surfactant, preferably an anionic or nonionic synthetic surfactant in an amount between about 0.2 to 5.0% by weight. Suitable anionic surfactants include fatty alcohol sulfates or fatty alcohol polyglycol ether sulfates in the form of the sodium, potassium, ammonium or alkanolammonium salts. The hydrogen peroxide in the preparation also may be stabilized with known additives for example such as dipicolinic acid, quinolinic acid, polyphosphates or the acylation products of phosphorous acid, such as 1-hydroxyethane-1,1-diphosphonic acid, e.g., see U.S. Pat. No. 3,122,417. Such stabilizers are included in the developer preparation in an amount between about 0.05 to 1.5% by weight. The aqueous developer prepartion is adjusted to a mildly acidic pH-value of approx. 2–5, preferably using acidic sodium pyrophosphate ($Na_2H_2P_2O_7$). In addition, fragrances and water-soluble protein derivatives may be added in order to improve cosmetic properties.

The developer dispersions of the present invention are mixed immediately before application with a distinctly alkaline dye base or bleach base. The alkalinity of the dye base or bleach base is sufficient to yield a mixture having a mildly alkaline pH of from about 8 to 10. The mixing ratio of the developer dispersion to the dye or bleach base typically is between about 2:1 to about 1:2 (parts by weight), depending on the original concentration of hydrogen peroxide in the developer dispersion and the desired effect as will be recognized by those skilled in the art.

The dye and bleach bases are generally provided as an emulsion, i.e., a cream-like emulsion of the oil-in-water type. The fatty phase preferably consists of fatty alcohols. These fatty alcohols are converted into a cream-like emulsion with water using an anionic emulsifier, preferably a fatty alcohol sulfate, or a fatty alcohol polyglycolether sulfate. However, nonionic emulsifiers also can be used, for example, such as adducts of ethylene oxide with fatty alcohols, fatty acids, fatty acid partial glycerides, sorbitan fatty acid esters or fatty acid alkanolamides. Suitable emulsion bases generally contain from about 7 to 15% by weight of fatty alcohol emulsified with from about 4 to 10% by weight of the above-mentioned emulsifiers (weight percents based on the emulsion as a whole).

In the case of the dye bases, oxidative dye precursors are incorporated in the emulsion base. In general, bleaching cream bases contain no oxidative dye precursors, although in certain cases a small amount of an oxidative dye precursor may be included as a dulling agent in order to compensate for the yellow or red luster which brown hair often assumes when it is bleached. The dye and bleach bases also contain an alkaline component, such as any of the previously identified aqueous bases. Preferably, the dye or bleach base contains a $NH_3$-solution and suitable buffer salts (ammonium salts), to provide a stable alkaline pH-value of approximately 9 to 11. Finally, the dye and bleach bases also contain relatively small quantities of perfumes and trichocosmetic agents, such as for example protein derivatives and cationic polymers.

When the dye and bleach bases are mixed with the developer dispersion ($H_2O_2$ preparation), the consistency of the cream base largely collapses. However, because of the alkaline pH-value spontaneously obtained in the mixture, the viscosity of the copolymer dispersion significantly increases, thus enhancing the viscosity of the mixture. Consequently, dye preparations or bleach preparations are obtained which can be applied readily to the hair with a brush or from an applicator provided with an appropriately shaped nozzle. Thus, known problems encountered when the consistency of the dye or bleach preparation is too low, particularly the problem of the dye or bleach preparation running along the hair and causing undesired dyeing or bleaching of certain parts of the hair, are successfully avoided. In addition, a brilliant dye finish is obtained using such preparations.

The following Examples are presented to illustrate further the present invention and are not intended to limit its scope which is defined by the attached claims.

EXAMPLE 1

A starting solution having the following composition was introduced into a reaction vessel:

62.5 parts by weight of water (fully deionized)

0.76 part by weight of nonylphenoxypolyethoxy(9 EO)-sulfosuccinate, disodium salt 0.76 part by weight of sodium alkyl($C_{12}$–$C_{18}$)polyethoxy(10 EO)sulfate 0.002 part by weight of ammonium peroxydisulfate One part by weight of dry ice ($CO_2$) was then added with slow stirring in order to establish an oxygen-free atmosphere in all parts of the apparatus.

A monomer mixture (feed solution I) was prepared by combining:

15.86 parts by weight of ethyl acrylate 10.00 parts by weight of methacrylic acid 2.86 parts by weight of acrylic acid 0.007 part by weight of ethylene glycol dimethacrylate and 0.29 part by weight of acetic acid anhydride This solution was introduced into a dropping funnel for feeding into the reaction vessel.

A second feed solution (feed solution II) was prepared by mixing:

4.58 parts by weight of water 1.14 parts by weight of nonylphenoxypolyethoxy(9 EO)sulfosuccinate, disodium salt 1.14 parts by weight of sodium alkyl($C_{12}$–$C_{18}$)polyethoxy(10 EO)sulfate 0.002 part by weight of ammonium peroxydisulfate This solution also was introduced into a dropping funnel for feeding into the reaction vessel.

After these solutions had been introduced into dropping funnels, another part by weight of dry ice was added to the reaction vessel so that an oxygen-free atmosphere was again established.

The starting solution was heated to about 75° C. and about 20% by weight of feed solution I was added to the reaction vessel. After about 5–10 minutes, an increase in the temperature of the reaction mixture to 78° C. indicated the start of the reaction. Over a period of about 25–30 minutes, feed solution II and the remaining 80% of feed solution I were slowly added simultaneously to the reaction vessel. The reaction temperature was maintained at about 80°–85° C. by cooling.

After all of feed solutions I and II had been added, the reaction mixture was stirred until the evolution of heat subsided, i.e., for about 20–30 minutes. A solution of 0.1 part by weight of water and 0.002 part by weight of ammonium peroxydisulfate then was added to the reaction vessel and the mixture was stirred for an additional 60 minutes at a temperature of 75° C. After cooling to 20° C., the copolymer dispersion was drained through a 250 um-mesh plastic sieve bag.

The dispersion had a solids content of 28.5% by weight. A solution was prepared by diluting a portion of the copolymer dispersion to a solids content of 1% by weight and adjusting its pH with $NH_3$ solution to a pH of about 8. This dilute solution had a viscosity at 20° C. of 2500 mPa.s (as measured with a Brookfield rotational viscosimeter at 20 r.p.m.).

EXAMPLE 2

A second copolymer dispersion was prepared by the same method used in Example 1. The only change was that the feed solution I consisted of:
15.86 parts by weight of ethyl acrylate
11.40 parts by weight of methacrylic acid
1.45 parts by weight of acrylic acid
0.007 part by weight of ethylene glycol dimethacrylate, and
0.29 part by weight of acetic acid anhydride.

A solution was prepared by diluting a portion of the resulting copolymer dispersion to a solids content of 1% by weight and adjusting its pH (with $NH_3$ solution) to a pH of about 8. The dilute solution obtained had a viscosity of 2200 mPa.s (measured at 20° C. in the manner of Example 1).

EXAMPLES 3–5

Three dye/bleach bases were prepared by blending the components listed in Table I in the indicated amounts. Three developer dispersions also were prepared by blending the components listed in Table 2 in the indicated amounts. Then the dye/bleach bases were mixed with the respective developer dispersions in the weight ratios noted in Table 3 and the viscosities of the mixtures were measured. The results are presented below.

TABLE 1

| Dye/Bleach bases | Example 3 Toner base (% by weight) | Example 4 Dyeing cream (% by weight) | Example 5 Bleaching cream (% by weight) |
| --- | --- | --- | --- |
| $C_{12}$–$C_{14}$ fatty alcohol +2 EO sulfate Na salt (28%) | 26.5 | 26.5 | 26.5 |
| $C_{12}$–$C_{18}$ fatty alcohol mixture | 10.5 | 10.0 | 12.0 |
| Oxidation dye precursors | 0.15 | 1.5 | — |
| Protein hydrolyzate | 0.10 | 0.10 | 0.15 |
| Perfume oil | 0.20 | 0.2 | 0.4 |
| $Na_2SO_3$ | 1.0 | 1.0 | — |
| $(NH_4)_2SO_4$ | 0.2 | 1.2 | 1.0 |
| $NH_4Cl$ | 0.45 | — | — |
| Water ($NH_3$—solution, pH 9.5) | Balance | Balance | Balance |

TABLE 2

| Developer dispersion | For Example 3 toner base (% by weight) | For Example 4 dyeing cream (% by weight) | For Example 5 Bleaching cream (% by weight) |
| --- | --- | --- | --- |
| $C_{12}$–$C_{14}$ fatty alcohol +2 EO sulfate Na salt (28%) | 2.0 | 2.0 | 2.0 |
| Protein hydrolyzate | 0.5 | 0.5 | 0.15 |
| 1-hydroxyethane-1,1-diphosphonic acid | 0.2 | 0.2 | 1.7 |
| $H_2O_2$ (35% solution) | 8.5 | 17 | 34 |
| Copolymer dispersion Example 1 | 8 | 10 | 6 |
| Water ($Na_2H_2P_2O_7$ to pH 3.8) | Balance | Balance | Balance |

TABLE 3

| | Example 1 | Example 2 | Example 3 |
| --- | --- | --- | --- |
| Mixing ratio of dye/bleach base to developer dispersion | 2:1 | 1:1 | 1:1 |
| Viscosity (20° C.) at $D = 6\ sec^{-1}$ ($\eta = \tau/D$) | 3950 mPa.s (20° C.) | 2866 mPa.s (20° C.) | 4266 mPa.s (20° C.) |

Although certain embodiments of the present invention have been described in detail, it will be appreciated that other embodiments are contemplated, along with modification of the disclosed features, as being within the scope of the invention, which is defined in the appended claims.

We claim:

1. An aqueous dispersion having a solids content of from about 5 to 30% by weight of a copolymer of ethyl acrylate, methacrylic acid, acrylic acid and as a crosslinking agent a polyethylenically unsaturated monomer, said copolymer consisting essentially of
   from about 50 to 60% by weibht of ethyl acrylate
   from about 30 to 40% by weight of methacrylic acid
   from about 5 to 15% by weight of acrylic acid and
   from about 0.02 to 0.04% by weight of said polyethylenically unsaturated copolymerizable monomer.

2. The aqueous dispersion of claim 1, wherein the polyethylenically unsaturated monomer contains at least two non-conjugated points of ethylenic unsaturation or at least two non-conjugated $CH_2{=}C{=}$ groups.

3. The aqueous dispersion of claim 1, wherein the monomer is either diethylenically or triethylenically unsaturated.

4. The aqueous dispersion of claim 3, wherein the monomer is diethylenically unsaturated.

5. The aqueous dispersion of claim 1 wherein said polyethylenically unsaturated monomer is selected from the group consisting of ethylene glycol dimethacrylate; trimethylolpropane trimethacrylate; polyethylene glycol dimethacrylate; 2-ethylhexane-1,3-dimethacrylate and allyl methacrylate.

6. The aqueous dispersion of claim 1 having a pH within the range of about 2 to 5 and a solids content of about 20 to 30% by weight of said copolymer.

7. The aqueous dispersion of claim 5 having a solids content of about 5 to 30% by weight of a copolymer consisting essentially of:
   about 55% by weight ethyl acrylate
   about 35% by weight methacrylic acid
   about 10% by weight acrylic acid and
   about 0.025% by weight ethylene glycol dimethacrylate.

8. A thickened aqueous composition comprising the aqueous dispersion of claim 1 and sufficient aqueous base to neutralize said copolymer.

9. The composition of claim 8, wherein the pH is at least about 8.

10. A thickened aqueous composition comprising the aqueous dispersion of claim 5 and sufficient aqueous base to neutralize said copolymer.

11. The thickened aqueous composition of claim 8 wherein said base is selected from the group consisting of sodium hydroxide, potassium hydroxide, monoethanolamine, diethanolamine and triethanolamine.

12. The thickened aqueous compostion of claim 10 wherein said base is selected from the group consisting of sodium hydroxide, potassium hydroxide, monoethanolamine, diethanolamine and triethanolamine.

13. A hydrogen peroxide preparation for use as a developer dispersion for oxidative hair dyes or for hair bleaches, comprising from about 1 to 20% by weight of hydrogen peroxide and from about 1 to 5% by weight of the copolymer dispersion of claim 1, said preparation having a pH-value of from about 2 to 5.

14. A hydrogen peroxide preparation for use as a developer dispersion for oxidative hair dyes or for hair bleaches, comprising from about 1 to 20% by weight of hydrogen peroxide and from about 1 to 5% by weight of the copolymer dispersion of claim 7, said preparation having pH-value of from about 2 to 5.

15. A method of thickening an aqueous medium which comprises adding to said aqueous medium the copolymer dispersion of claim 1 and sufficient aqueous base to neutralize said copolymer.

16. The method of claim 15 wherein said base is selected from the group consisting of sodium hydroxide, potassium hydroxide, monoethanolamine, diethanolamine and triethanolamine.

17. A method of thickening an aqueous medium which comprises adding to said aqueous medium the copolymer dispersion of claim 5 and sufficient aqueous base to neutralize said copolymer.

18. The method of claim 17 wherein said base is selected from the group consisting of sodium hydroxide, potassium hydroxide, monoethanolamine, diethanolamine and triethanolamine.

19. A method of thickening an aqueous medium which comprises adding to said aqueous medium the copolymer dispersion of claim 6 and sufficient aqueous base to neutralize said copolymer.

20. A method of thickening an aqueous medium which comprises adding to said aqueous medium the copolymer dispersion of claim 7 and sufficient aqueous base to neutralize said copolymer.

21. The method of claim 19 wherein said base is selected from the group consisting of sodium hydroxide, potassium hydroxide, monoethanolamine, diethanolamine and triethanolamine.

22. The method of claim 20 wherein said base is selected from the group consisting of sodium hydroxide, potassium hydroxide, monoethanolamine, diethanolamine and triethanolamine.

23. A method of preparing an oxidative hair dye or hair bleach comprising blending with an oxidative dye emulsion or bleach emulsion containing an aqueous base the hydrogen peroxide preparation of claim 13.

24. A method of preparing an oxidative hair dye or hair bleach comprising blending with an oxidative dye emulsion or bleach emulsion containing an aqueous base the hydrogen peroxide preparation of claim 14.

* * * * *